United States Patent [19]

Franz

[11] Patent Number: 4,609,675

[45] Date of Patent: Sep. 2, 1986

[54] STABLE, HIGH DOSE, HIGH BULK DENSITY IBUPROFEN GRANULATIONS FOR TABLET AND CAPSULE MANUFACTURING

[75] Inventor: Robert M. Franz, Otsego Township, Allegan County, Mich.

[73] Assignee: The Upjohn Company, Kalamazoo, Mich.

[21] Appl. No.: 661,538

[22] Filed: Oct. 16, 1984

Related U.S. Application Data

[63] Continuation-in-part of Ser. No. 641,917, Aug. 17, 1984, abandoned.

[51] Int. Cl.$^4$ .......................... A61K 9/16; A61K 9/34
[52] U.S. Cl. ...................................... 514/568; 514/770; 514/781
[58] Field of Search ......................................... 514/568

[56] References Cited

U.S. PATENT DOCUMENTS

| | | | |
|---|---|---|---|
| 3,379,721 | 4/1968 | Reid | 536/88 |
| 3,679,794 | 7/1972 | Bentholm et al. | 536/98 |
| 4,068,068 | 1/1978 | Holst et al. | 536/88 |
| 4,145,440 | 3/1979 | Fitch et al. | 424/287 |
| 4,200,736 | 4/1980 | Shinohara et al. | 536/88 |
| 4,200,737 | 4/1980 | Marder et al. | 536/88 |
| 4,209,512 | 6/1980 | Torode et al. | 424/228 |
| 4,215,117 | 7/1980 | Shah et al. | 424/248.4 |
| 4,248,595 | 2/1981 | Lask et al. | 536/88 |
| 4,250,306 | 2/1981 | Lask et al. | 536/88 |
| 4,337,273 | 6/1982 | Lefer | 514/568 |
| 4,340,731 | 7/1982 | Colombo et al. | 536/88 |
| 4,361,580 | 11/1982 | Peck et al. | 514/777 |
| 4,404,371 | 9/1983 | Bellmann et al. | 536/98 |
| 4,439,453 | 3/1984 | Vogel | 514/781 |
| 4,521,594 | 6/1985 | Kanematu | 536/88 |

OTHER PUBLICATIONS

A group of Derwent Abstract card copies, on numbered pp. 2 to 20, disclosing drug formulations, some with Ibuprofen.

Third Supplement to USP XX and to NF XV (1982) pp. 367-368.

PCT International Application No. PCTUS80/00235; International Pub. No. WO 81/02521, published Sep. 17, 1981.

Mallinckrodt brochure (2 pages) for 90% Acetaminophen/10% Starch COMPAP Product.

Primary Examiner—Ronald W. Griffin
Attorney, Agent, or Firm—John T. Reynolds

[57] ABSTRACT

Dry granulate pharmaceutical compositions containing 85 to 99 percent by weight of ibuprofen and 1 to 15 percent, by weight of Croscarmellose sodium, types A and/or B (cross-linked sodium carboxymethylcellulose) are useful for making ibuprofen compressed tablet and filled capsule formulations containing from about 100 to about 1200 mg. of ibuprofen per dosage unit. They are particularly helpful for making compressed tablets containing from 800 to 1200 mg. of ibuprofen per tablet, which have bioavailability rates similar to those of presently known lower dosage strength ibuprofen tablets.

9 Claims, 9 Drawing Figures

FIG. 2 - EXAMPLE 3

FIG. 3 - EXAMPLE 3

STABLE, HIGH DOSE, HIGH BULK DENSITY IBUPROFEN GRANULATIONS FOR TABLET AND CAPSULE MANUFACTURING

CROSS-REFERENCE

This is a continuation-in-part of application Ser. No. 641,917, filed Aug. 17, 1984, now abandoned.

INTRODUCTION

This invention relates to pharmaceutical granulation formulations or compositions of ibuprofen, the generic name for 2-(4-isobutylphenyl)-propionic acid. More particularly, this invention provides new ibuprofen dry granulation formulations containing a high percentage content of ibuprofen per se, so that compressed tablets and capsules manufactured using these new formulations are smaller in volume than what would be expected from current ibuprofen pharmaceutical formulations. These new ibuprofen dry granulation formulations allow manufacturing of ibuprofen drug in the form of pharmaceutical tablets and capsules which have excellent dissolution properties and physical stability, increased "age" resistance to dissolution rate lowering, high ibuprofen content, high bulk density, excellent bioavailability and excellent manufacturing processing properties, including good granulation flowability, minimal or diminished tablet punch or plunger-sticking during compressing or capsule filling and good compression characteristics.

BACKGROUND OF THE INVENTION

Ibuprofen per se is a poorly water soluble drug with a melting point in the 75°-77° C. range. Ibuprofen is prescribed and sold, and now sold over-the-counter, as a pain relieving, fever-reducing and antiinflammatory drug. In some patient populations ibuprofen must be taken regularly in dosages up to or greater than about 3200 mg./day to alleviate the pain or other symptoms associated with the inflammatory disease being treated. The implications of these daily dosages is that a patient must take large amounts of ibuprofen in the form of tablets or capsules to maintain the desired effective dose of ibuprofen each day.

Currently, ibuprofen is formulated for sale by manufacturers in coated compressed tablets containing from 200 mg. to 600 mg. of ibuprofen per tablet. Those in the art would like to have higher dose ibuprofen tablets or capsules so that the patient needing same would only have to take a minimal number of tablets or capsules to maintain the desired dosage of ibuprofen per day regimen. This would also aid in patient compliance with the medication.

Manufacturers of ibuprofen formulations would also desire to prepare one ibuprofen granulation formulation which is adaptable to further processing with or without the addition of acceptable pharmaceutical excipients such as lubricants, diluents and binders for formulation of the high ibuprofen content, final, finished tablet or filled capsule dosage form, in a variety of dosage strengths as desired by marketers, physicians, pharmacists and patients.

However, the chemical and physical properties of ibuprofen, per se, the physical form it is obtained from ibuprofen per se suppliers thereof, the need for large volumes of ibuprofen per se and pharmaceutical formulations thereof to satisfy the need and market therefor, the current wet granulation and direct compression formulation methods are unsuitable for making large percentage (over 73% by weight) high dose ibuprofen pharmaceutical tablet formulations for patients and drug manufacturers alike for a number of reasons. Low bulk density of ibuprofen per se, as it is currently obtained from chemical suppliers thereof causes the need for rather large tablet and capsule forms of the final high dose pharmaceutical formulations of such low density ibuprofen. The size of the punches of the tablet making machines must be correspondingly large to obtain the necessary fill weight. Attempts to minimize the inclusion of desirable pharmaceutical excipients to keep the size of the punch and tablet (or capsule) size down results in tablets with undesirable properties. Extrapolating these manufacturing difficulties to the making of pharmaceutically "elegant" high dose ibuprofen tablets (i.e., greater then 800 mg.) by currently known wet granulation techniques only emphasizes that there will be obtained a large ibuprofen tablet that will be difficult for some patients to swallow and thus be unacceptable to them, and thus to the progression of decision makers in the course of manufacturing such an ibuprofen tablet or capsule product.

Moreover, currently produced ibuprofen wet granulation formulations tend to "age" over time, as the tablets or capsules sit in warehouses and drugstore shelves, thereby lowering the rate of dissolution of the ibuprofen. This 'aging' property is illustrated by accelerating this 'aging' under conditions of high temperature (40°-60° C.) and/or humidity in laboratory studies. This aging phenomenon appears as a decrease in the in vitro dissolution rate of the ibuprofen-containing product by standard test methods. This reduction in dissolution rate has been theorized as being attributed to the scintering of the bulk ibuprofen. Scintering is a type of "cementing" of the ibuprofen drug particles to one another. The thermal mobility of the surface ibuprofen molecules is believed to increase as temperature of the ibuprofen particles is increased to approximately one-half to two-thirds of the melting point of ibuprofen (Ibuprofen MP—75°-77° C.). This increased mobility of the ibuprofen particles is believed to result in diffusion of the ibuprofen molecules between contact points in the formulation being tested. (See W. Pietsch, "Fundamentals of Agglomeration", an industrial workshop presented at the Powder and Bulk Solids Conference/Exhibition, Chicago, Ill., USA, in May, 1984.) As a result of this scintering, solid ibuprofen bridges are formed between ibuprofen particles which effectively reduce the ibuprofen drug surface area available for dissolution over time. Other drug substances have exhibited the same lowering of dissolution rate over time phenomenon and some have required special manufacturing and/or formulation procedures to minimize the drug particle-to-drug particle contact or scintering thereof.

A typical way in the pharmaceutical formulation art to minimize scintering of drug molecules in a solid drug formulation has been to increase the level or percentage of excipients or diluents in order to further isolate the individual drug particles from one another. This excipient increase or further dilution action becomes prohibitive where it is desired to make high drug percentage content ibuprofen drug formulations, i.e., high dose tablets or filled capsules, because such tablets or capsules made from currently used wet granulation ibuprofen formulations result in final tablets or capsules which are too large to be acceptable to the majority of the patient population which might otherwise desire this large dose of ibuprofen.

Attempts to make active drug granulations into a higher bulk density physical form in order to reduce the volume or size of tablet or capsule needed for a desired dosage per unit has been tried, but with ibuprofen, some methods normally used to increase bulk density per unit volume of drug actually promote scintering or "cementing" of the drug thereby adversely affecting the drug dissolution rate.

In doing the research which led to this invention approximately fifty pharmaceutical formulations containing ibuprofen as the high percentage content active drug component therein were tried before this invention was recognized or definable, and an acceptable ibuprofen dry granulation prototype formulation described and claimed herein was developed. The major problems with the majority of those approximately fifty ibuprofen formulations were:

1. Inadequate bulk density of the ibuprofen granulations to obtain a reasonably sized tablet.
2. Punch filming, picking or sticking during compression of the resulting ibuprofen granulations.
3. Poor flowing granulation formulations, which are difficult to handle in typical pharmaceutical plant scale equipment.
4. Excessive disintegration times of tablets made from the ibuprofen granulations.
5. Lamination and friability problems with tablets made from the ibuprofen granulations.
6. The use of alcohol, e.g., ethanol, as part of a wet granulation ibuprofen premix preparation, requires special equipment in a pharmaceutical plant, which would be desirably avoided.
7. Because of the high dosage strengths involved, only minimal amounts of pharmaceutical excipients could be added to overcome the above problems (i.e., punch filming, poor flow, excessive disintegration times, lamination, etc.) In addition, besides the above problems facing an industrial pharmacist or pharmaceutical engineer, there is the concern that in some cases, the source of supply of certain types of the bulk ibuprofen drug per se may not be reliable or dependable. Thus, the industrial pharmacist or pharmaceutical engineer must discover process conditions, choices and proportions of ingredients to process available sources of ibuprofen to make processable high ibuprofen drug content dry granulation formulations and final formulations (i.e., tablets and capsules) which will overcome the above problems, acceptable to the pharmaceutical industry, physicians and the pharmacists and patient populations alike.

A Torode et al U.S. Pat. No. 4,209,513 discloses a wet water and alcohol granulation method for making a compressed tablet containing a high content (80% to 98%, W/W) of a combination of a 2,4-diaminopyrimidine and a sulfonamide antimicrobial drug formulation containing not more than 20% W/W of a granulating and disintegrating agent, the combination having a particle size less than 40 micrometers, and the disintegrating agent having a swelling capacity greater than 5 ml./gram. However, the brand named disintegrating agents referred to therein, including those for the low viscosity sodium carboxymethylcellulose such as Capagel, and the starch, cellulose derivatives, gelatin and polyvinylpyrrolidine granulating agents, referred to therein are not effective in obtaining the ibuprofen dry granulation formulations described herein. Moreover, the use of alcohol now requires special explosion and fireproof equipment that is expensive and best avoided if possible.

Those in the art continue to do research to find improved cost efficient methods for preparing uniform high percentage ibuprofen granulation formulations which are adaptable for further use in compounding a number of desirable high strength ibuprofen drug end product forms and sizes which will still have all of the above stated chemical and physical properties and be acceptable to patients.

DRAWINGS AND FIGURES

FIG. 1 is an ordinate/abscissa graph depicting the dissolution rate differences of film coated compressed tablets (FCT) of 800 mg. ibuprofen manufactured from the described dry granulation of this invention, with the dissolution rate of sugar coated compressed tablets (SCT) of ibuprofen, 400 mg. (commercial "wet granulation" method) over a thirty minute period. See Example 3. Dissolution was performed using the current USP dissolution test (i.e., 150 RPM basket).

FIG. 2 is an ordinate/abscissa graph depicting the effect on a USP dissolution rate test (at a 50 RPM dissolution test basket speed) of four percentage level amounts of the intragranular disintegrant (cross-linked sodium carboxymethylcellulose, "Croscarmellose Sodium NF, type A") on dry granulation prepared 800 mg. ibuprofen compressed tablets of this invention, and compared with the dissolution rate of a 200 mg. ibuprofen film coated compressed tablet (FCT) (manufactured using a wet granulation) over 35 minutes. See Example 3.

Figure 9:
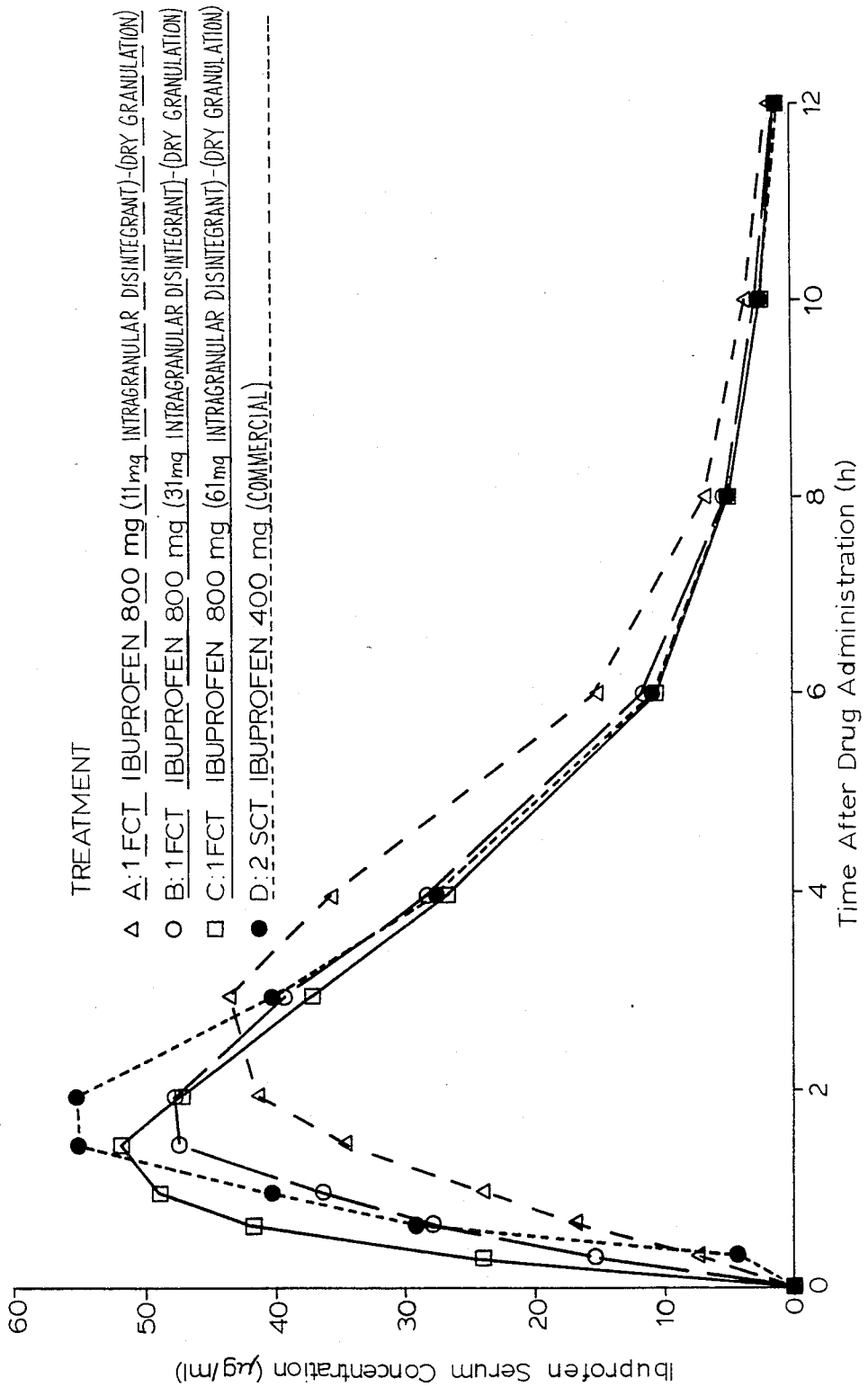

FIG. 9 is an ordinate/abscissa graph of curves showing the effect on mean ibuprofen blood serum concentrations following the administration of single oral 800 mg. ibuprofen dosage tablets compressed from the dry granulation formulas of this invention containing 11 mg., 31 mg. or 61 mg. of the intragranular disintegrant, sodium carboxymethylcellulose (Croscarmellose Sodium, type A) to 22 normal, healthy, human volunteers over 12 hours as compared to commercially available 400 mg. ibuprofen tablets (wet granulation).

OBJECTS OF THE INVENTION

It is an object of this invention to provide ibuprofen dry granulation, high drug content, high bulk density formulations which are adaptable for further processing to make a range of solid dosage unit strength forms of ibuprofen in smaller sized compressed tablet or filled capsule forms, than are available with currently used wet granulation methods.

It is a further object of this invention to provide new high ibuprofen percentage content, dry granulation formulations which have improved manufacturing, dissolution, stability and bioavailability properties compared to commercially available products.

Other objects, aspects and advantages of this invention will be apparent from the remaining specification and the claims which follow.

SUMMARY OF THE INVENTION

Briefly, this invention provides new pharmaceutical dry granulation, high ibuprofen drug content granulation formulations which are adaptable to final formulations having a variety of dosage forms such as compressed tablets and filled capsules, and dosage sizes ranging from 100 to 1200 mg. per dosage unit, and which final drug forms (resulting from the new dry granulation formulations) will have specific advantageous properties including (a) excellent physical stability, especially regarding compressed tablets dissolution properties, (b) high dosage of active drug, ibuprofen, (c) high bulk density, (d) excellent bioavailability and (e) excellent processing properties in pharmaceutical plant equipment including good flowability, minimal tablet punch or plunger sticking during compressing or capsule filling, and good compression characteristics. These new dry granulation and final ibuprofen formulations have been particularly adapted for the making of manufacturable and patient acceptable form of 800 mg. ibuprofen tablets for administration of four such tablets per day to patients in need of a 3200 mg. of ibuprofen per day regimen of ibuprofen, but this invention is not limited thereto.

DETAILED DESCRIPTION OF THE INVENTION

This invention provides new dry granulation pharmaceutical, high ibuprofen drug content, formulations or compositions comprising ibuprofen USP from 85.00 to 99.0 percent and Croscarmellose sodium NF, types A and B (internally cross-linked carboxymethylcellulose, NF) from 1.00 to 15.00 percentages of each ingredient being on a weight/weight basis, based upon the weight of the total composition. These new dry granulation high ibuprofen content compositions also preferably include from about 0.4 to 1 percent of colloidal silicon dioxide NF, based upon the weight of the total granulation formulation. They can also optionally include from about 0.25 to about 2.5 percent, on a weight/weight basis of a lubricant, such as magnesium stearate in the granulate formulation.

These high ibuprofen content granulation formulations are preferably prepared by (1) dry mixing (a) an ibuprofen and (b) croscarmellose sodium NF-containing mixture to an essentially uniform consistency, and then (2) running this mixture through a roller compactor, e.g., a chilsonator, or by slugging the dry powder mixture into slugs, and then (3) sizing the compacted or slugged mixture through a series of screens (recycling large and small particles) to form a granulate ibuprofen composition of fairly uniform granule size.

This invention further provides pharmaceutical, bulk dry granulation drug compositions useful for making extensive numbers of compressed tablets or filled capsules containing desired dosage unit strength forms containing from about 100 mg. to 1200 mg. of ibuprofen per dosage unit which may or may not comprise mixing one of the above high percentage content ibuprofen dry granulation formulations with further extra granular excipients. The weight amounts of such additional dry excipients in a tablet formulation should total not more than about 27 percent by weight, based upon the weight of the resulting total composition. For example, a pharmaceutical ibuprofen dry granulate composition which is adopted for making extensive numbers of compressed tablets therefrom, each compressed tablet nominally containing approximately 800 mg. of ibuprofen can be made by mixing (A) a dry granulate composition containing:

| Ingredient | Amount to Equal Mg./Tablet |
|---|---|
| Ibuprofen USP | 800 ± 10% (720 to 880) |
| Croscarmellose sodium NF, Type A | 54 to 67 |
| Colloidal silicon dioxide, NF | 7 to 9 |
| Magnesium stearate | 0.5 to 1.5 | which dry granulate composition is then further mixed to essentially uniform consistency with the following additional (B) extragranular ingredients:

| Extragranular Ingredients | Amount to Equal Mg./Tablet |
|---|---|
| Croscarmellose sodium NF, type A | 13 to 17 |
| Microcrystalline cellulose, NF | 170 to 210 |
| Colloidal silicon dioxide NF and | 13 to 17 |
| Talc, NF No. 141 | 8 to 12 |

Further, for example, for a compressed tablet final formulation to contain a nominal average amount 1000 mg. of ibuprofen per tablet, a dry granulate formulation mixture (A) designed to produce tablets containing 1000 mg. of ibuprofen, 76.25 mg. of intragranular croscarmellose sodium NF, type A, 10 mg. of intragranular colloidal silicon dioxide NF and 1.25 mg. of an intragranular lubricant such as magnesium stearate, the actual amounts of which can range per tablet from 900–1100 mg. of ibuprofen, 68–84 mg. of croscarmellose sodium NF, type A, 9 to 11 mg. of colloidal silicon dioxide NF and 0.75 to 1.75 mg. of magnesium stearate, in the end product compressed tablet, is further mixed with (B) a variety of pharmaceutical excipients such as the following additional extragranular ingredients:

| Ingredient | Amounts to Equal Mg./Tablet |
|---|---|
| Croscarmellose sodium NF, type A | 13 to 17 |
| Colloidal silicon dioxide | 3 to 7 |
| Talc NF | 10 to 15 | to a uniform consistency, and then the resulting granule containing composition is compressed into the required size tablets to contain 1000 mg. of ibuprofen per tablet.

These dry granulate high ibuprofen content compositions are also adaptable to use in filling gelatin capsules to contain the desired amount of ibuprofen per capsule. For example, a dry granulate composition A containing 190–210 mg. of ibuprofen 13.5 to 16.5 mg. of croscarmellose sodium NF, type A, 1.5 to 2.5 mg. of colloidal silicon dioxide NF and 0.2 to 0.3 mg. of magnesium stearate, can be further, optionally mixed with the following additional extragranular ingredients:

| Ingredients | Amount to Equal Mg./Capsule |
| --- | --- |
| Magnesium stearate, NF (powder, food grade) | 5 to 7 |
| Mineral Oil USP (viscosity 160–200 cps) | 6 to 8 |
| Microcrystalline cellulose NF (medium powder) | 100 to 110 |
| Pregelatinized starch NF | 60 to 80 | to a uniform consistency. This resulting dry granule containing composition can then be used to fill gelatin capsules sized to contain about 200 mg. of ibuprofen per capsule.

Another aspect of this invention is a process for preparing a pharmaceutical ibuprofen granulate composition, which is useful for further processing as described herein, for making compressed tablets or filled capsules containing from about 100 to 1200 mg. of ibuprofen per dosage unit which comprises (1) dry mixing a composition containing ibuprofen and croscarmellose sodium NF in proportions of from about 85 to 99 percent, W/W of ibuprofen, based upon the weight of the total mixture, to about 1 to 15 percent W/W croscarmellose sodium NF to essentially uniform consistency (2) passing the mixture from step (1) through a roller compactor or a slugging operation, and (3) screening the resulting compacted or slugged composition from step (2) through a vibratory sieve or series of screens to form a granulate of essentially uniform size granules.

The dry mixture composition mixed in step (1) of the process also preferably includes from about 0.4 to about 1 percent W/W of colloidal silicon dioxide NF, based upon the weight of the total granulate composition.

The term "intragranular", when used in connection with sodium cross-linked carboxymethylcellulose, colloidal silicon dioxide, and magnesium stearate NF powder food grade means these ingredients are found within the dry granule structure itself. The term "extragranular" means the material is located externally to granule structure. Typically, acceptable extragranular pharmaceutical excipients are optionally added dry to the final dry granulation in the form of additional disintegrants, lubricants, powder flow promoters and binders.

The croscarmellose sodium NF, types A and B, used herein are a type of cross-linked sodium carboxymethylcellulose. They function for this invention at very low weight percentage levels in these dry granulation formulations to afford effective disintegration of the dry compacted granules in any dosage form into which they are put, that is, in compressed tablet or filled capsule. They are described in the *THIRD SUPPLEMENT TO USP XX AND TO NF XV* (1982), pp. 367–368. Croscarmellose sodium NF, types A and B, are available commercially under tradenames "CLD-2" (type B) sold by Buckeye Cellulose Co., and the tradename "Ac-Di-Sol" (type A) sold by Farm Machinery Corporation.

We believe our findings here of the combination of high ibuprofen content and the cross-linked sodium carboxymethylcellulose NF, prepared as described herein, giving dry granulation premix formulations having the above manufacturing, stability and bioavailability advantages and the resulting final formulations therefrom suitable for compressed tablet and filled capsule pharmaceutical properties is unexpected because several other dry granulation formulations of "super disintegrant" and classical disintegrant materials available on the market yielded unacceptable results in terms of one or more of the above manufacturing, pharmaceutical or tablet size properties. For example, the following additional disintegrants were tried without success:

1. Crospovidone NF (cross-linked homopolymer of N-vinyl-2-pyrrolidinone) sold as Polyplasdone XL-10 by GAF Corp.

2. Cornstarch NF, sold by various suppliers.

The excellent in vitro ibuprofen release rates observed in standard pharmacy tests with tablets and capsules manufactured using these high dose ibuprofen dry granulations, even after accelerated aging, have been documented and are exemplified in a detailed example hereinbelow. Compressed tablets manufactured using the dry granulation techniques described herein have also been shown to have excellent bioavailability properties, which is exemplified below in a detailed example. One coated compressed 800 mg. ibuprofen formulation, made by the methods described herein, has proven to have statistically significantly higher ibuprofen blood serum concentrations, at times less than an hour after administration than a currently marketed, wet granulation method, coated compressed tablet of ibuprofen (MOTRIN ®, tablets 400 mg., UPJOHN).

The following advantages and improvements over currently known technology flow from this invention.

A. High dose (85%–99% ibuprofen) high bulk density (at least 0.4 g./ml., untapped, and at least 0.5 g./ml. tapped) ibuprofen dry granulation formulations which can be manufactured using the techniques or processes described herein that can then be incorporated into tablet and capsule end product pharmaceutical formulations with or without typical pharmaceutical adjuvants that result in ibuprofen dosage forms having reasonable tablet and capsule size limits that aid in patient acceptance.

B. The dry granulation formulations and the processing procedures of this invention described herein allow these high ibuprofen content dry granulation formulations to be manufactured using roller compaction or slugging with a minimum of ibuprofen scintering, as evidenced by the excellent dissolution and bioavailability data results obtained.

C. The new ibuprofen dry granulation formulation and processing parameters described herein also minimize further ibuprofen scintering, i.e., they stabilize the ibuprofen formulation with regard to dissolution rate properties during storage at accelerated conditions as evidenced by the changes in dissolution rates over time when compared to currently available marketed ibuprofen products.

D. The ibuprofen dry granulations produced by the processing steps disclosed herein have excellent flow properties (unlike the bulk ibuprofen drug currently obtained from suppliers thereof); they minimize sticking and filming on final composition punch and plunger faces and have good compressing and filling characteristics with or without minimal amounts of the additional extragranular excipients.

The granulation formulations of this invention are primarily dry granulations, that is, the bulk ibuprofen, croscarmellose sodium NF, types A and B, and other possible ingredients for the granules are mixed without adding any additional liquid of any kind. However, it is intended to include as part of this invention powdered ingredients of the described types which may have water of hydration therein, and other lightly wetted powders that act essentially the same in mixing as powder mixtures to which no external liquid has been added.

Figure 7:
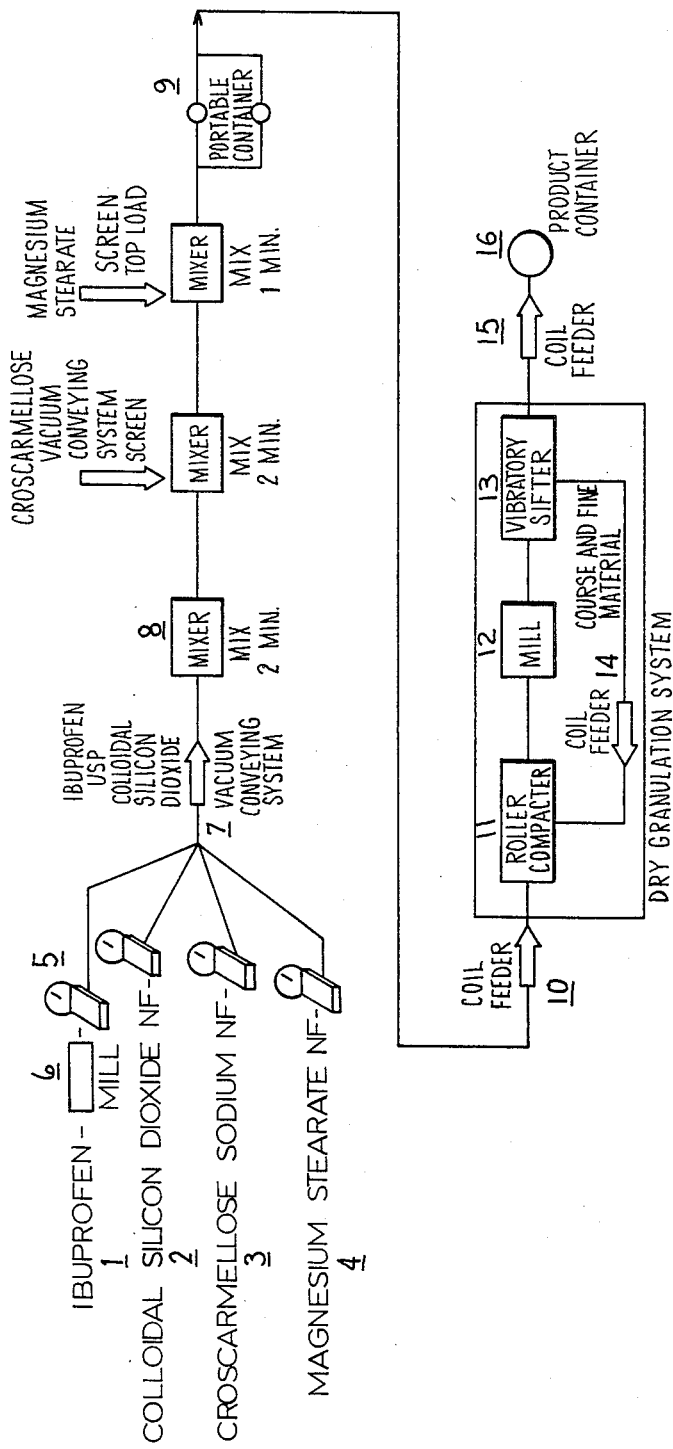
FIG. 7 is a simplified schematic flow sheet depicting a proposed manufacturing process for making a high percentage ibuprofen dry granulation formulation of this invention.
Figure 8:
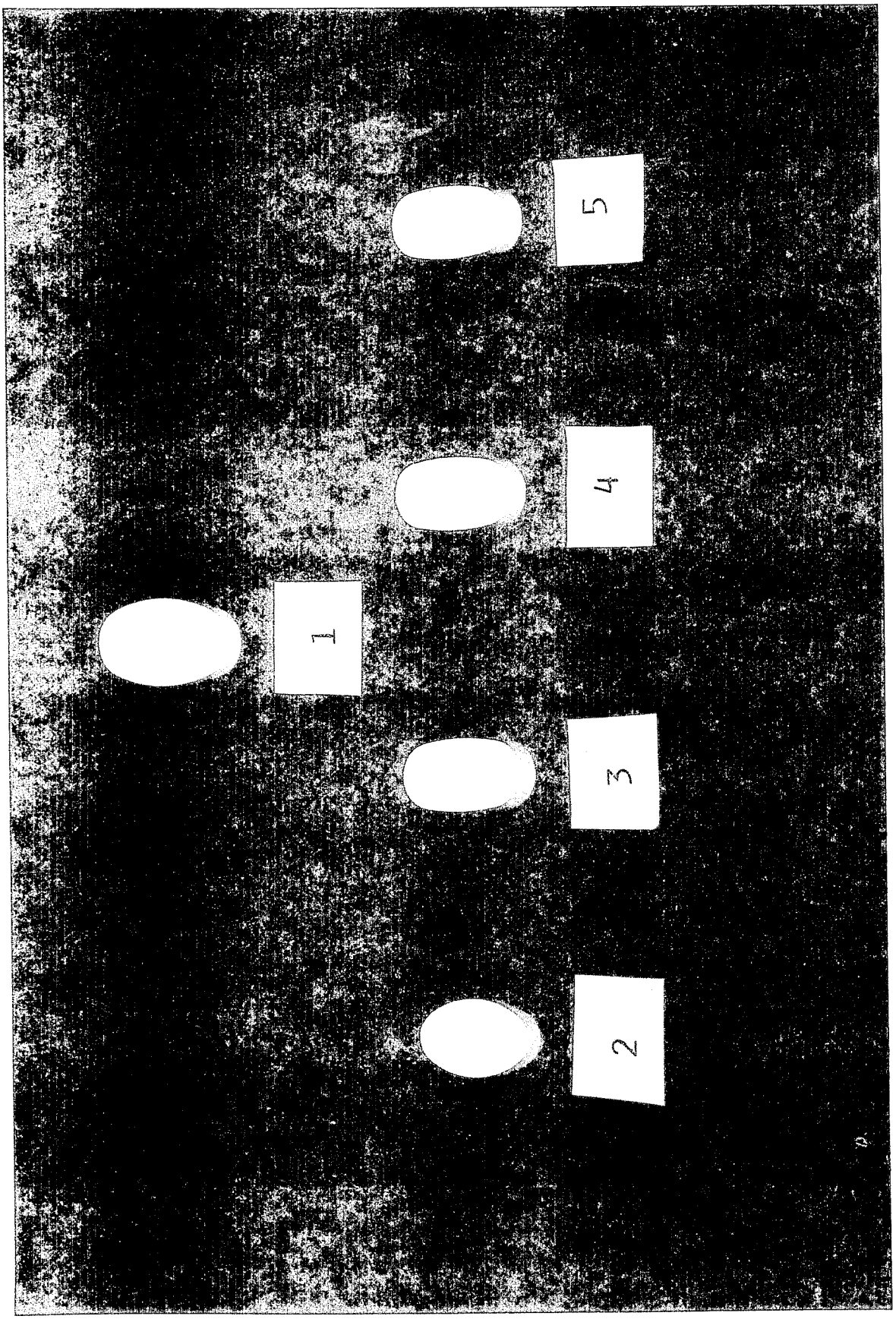
FIG. 8 is a photoprint comparing the relative sizes of an 800 mg. ibuprofen compressed tablet made using the commercial wet granulation formulation (1) to 600 mg. (2), 800 mg. (3), 1000 mg. (4) and 1067 mg. strength compressed ibuprofen (5) tablets manufactured using the dry granulation formulation of this invention.

FIG. 7 illustrates in a simplified schematic flow sheet form an example of a proposed process for manufacturing the ibuprofen dry granulate composition of this invention. The selected bulk ingredients, here, ibuprofen USP (1), colloidal silicon dioxide NF (2), croscarmellose sodium NF (3) and magnesium stearate (4), are separately weighed on a scale 5, and conveyed 7 to the mixer, as needed. The bulk ibuprofen, from the supplier is sifted through an appropriate mill 6 into the tared weighing container. The milled bulk, weighed ibuprofen 1 is conveyed by a vacuum conveying system 7 to a mixer 8, followed by the addition of the colloidal silicon dioxide 2. The ibuprofen 1/silicon dioxide 2 mixture is mixed for two minutes and then the weighed amount of the croscarmellose sodium NF 3 is added to the mixer 8 by a vacuum conveying system 7, and the resulting composition is mixed for two more minutes. Then, the magnesium stearate 4 is added to the mixer through a screen and the resulting mixture is mixed for one additional mimute. The resulting dry mixed powder mixture is then conveyed by a portable container 9 to the location of a roller compactor/hammer mill/vibratory sifter (series of screens) apparatus. The above powder mixture can be fed to he roller compactor 11, from which the compacted mixture passes through a hammer mill 12, and then the mixture falls through the vibratory sifter 13. The sifter is fitted with conveying apparatus 14 to recycle coarse and fine granulate material back through this compactor/mill/sieve cycle to help form dry granules of essentialy uniform granule size. The bulk dry granular product from this operation is conveyed via a coil feeder 15 to a temporary bulk dry granulation product container. From this operation the dry granulation product can be taken directly to a tablet compressing or capsule filling operation room, or can be blended further with additional optional ingredients such as are described in the detailed examples, in a blender such as a V-blender of the appropriate size, and then the resulting final dry granulation formulation can be compressed into tablets or filled into capsules of the desired dosage strength.

EXAMPLE 1

A. 1000 mg. Ibuprofen Drug Delibery System

The following two major part (dry granulation Part and extragranular excipient part) formula was prepared as described hereinbelow as a proposed drug delivery system for 1000 mg. ibuprofen tablet formulation:
Dry Granulation Part:
Ibuprofen USP 1000.0 mg.
Colloidal Silicon Dioxide, NF 10.0 mg.
Croscarmellose, Sodium, NF, Type A 76.25 mg.
Magnesium stearate NF (powder, Food Grade) 1.25 mg.
Extragranular Excipients:
Colloidal Silicon Dioxide, NF 5.0 mg.
Croscarmellose Sodium NF, Type A 15.0 mg.
Talc, USP 12.5 mg.

The above listed materials under Dry Granulation part were mixed in bulk in the above proportions for the number of proposed tablet dosages to be made per batch in the equipment available.

These dry granulation materials are added to and mixed in an appropriate mixer in the order listed to an essentially uniform consistency. This preliminary mixing process accomplishes:

1. coating of the bulk drug, ibuprofen with colloidal silica, and 2. an intimate dispersion of the cross-linked sodium carboxymethylcellulose with the bulk drug, ibuprofen.

The Dry Granulation Part mixture is then run through a roller compactor or slugged, and then milled and sieved through a series of screens to form uniform granules. The granules are then added to the Extragranular Excipient Part ingredients in a V-shaped blender and mixed to a uniform consistency. The resulting mixed material is then passed through a tableting machine where the mixture is compressed into 1000 mg. ibuprofen content tablets using 0.7446 inch by 0.378 inch (1.891 centimeters by 0.960 centimeters) elliptical tablet shaped punch tooling. The dissolution rate results for these 1000 mg. ibuprofen tablets were as shown below.

The dissolution profiles for ibuprofen released from the 1000 mg. tablets were collected using a Hanson Multiple Spindle Dissolution Apparatus employing 1125 mls. of 0.05M $KH_2PO_4$ dissolution media in each flask. The setup and operation are outlined below:
Water Bath—37° C.
Basket RPM—50 RPM
Flow Rate—45 ml./min.
Wavelength—221.0 nm
Cell Width—0.10 mm.
Temperature Control—37° C.

A 50 RPM basket speed was used to make the test more discriminating. The average results of three tablets were used for calculating all data points. The results, presented below, show that, even with minimal quantities of excipients, excellent dissolution properties are obtained using the dry granulation of this invention.

| Time (min) | Average Percent Dissolved |
| --- | --- |
| 0.3 | 0 |
| 3.3 | 13.3 |
| 6.3 | 45.9 |
| 9.3 | 79.8 |
| 12.3 | 90.3 |

The physical properties of these 1000 mg. ibuprofen compressed tablets were are follows:
Thickness: 0.335 inches
Hardness: 26.9 Strong Cobb Units
Friability: 0.21 percent
Disintergration time: 1 minute, 5 seconds
Appearance: Excellent

EXAMPLE 2

800 mg. Ibuprofen Dry Granulation

This example illustrates how to make an 800 mg. per tablet ibuprofen formulation composition according to this invention which is bioequivalent to two 400 mg. commercially available coated compressed tablets of ibuprofen, which commercial ibuprofen tablets were prepared from currently used wet granulation procedures of a mixture of:

| Ingredient | Percent, W/W |
| --- | --- |
| Ibuprofen | 67.91 |
| Corn Starch, NF, bolted | 28.01 |
| Colloidal Silicon Dioxide, NF | 0.34 |
| Pregelatinized Starch NF, bolted | 3.74 |
| | 100.00 |

For a desired number of 800 mg. ibuprofen dosage tablets, the equivalent multiple weight amounts of the following ingredients are first intimately dispersed using an appropriate mixer to a uniform consistency:

| Ingredient | Mg. Per Compressed Tablet |
| --- | --- |
| Ibuprofen | 800 |
| Croscarmellose Sodium, NF, type A | 61.00 |
| Colloidal Silicon Dioxide NF | 8.00 |
| Magnesium Stearate NF (powder, food grade) | 1.00 |

Our procedure has been to first mix the ibuprofen and the colloidal silicon dioxide for two minutes in an appropriate blender. Then the Croscarmellose Sodium, NF is added to the blender and the resulting powder mixture is mixed dry for two more minutes. Then the optional magnesium stearate is added through a screen to the blender. The resulting mixture is mixed dry for another one minute.

The mixed dry granulation materials are then passed through a roller compactor or slugged, then run through a hammer mill (Fitzmill) and then through a vibrating sifter (a series of screens) to obtain a uniform granulate.

The above dry granulation formulation is then blended in a V-blender with the following additional extragranular ingredients for ten minutes prior to storage awaiting compression into tablets.

| Extragranular Ingredient | Mg./Compressed Tablet |
| --- | --- |
| Microcrystalline Cellulose NF, Coarse Grade | 190.0 |
| Colloidal Silicon Dioxide NF | 15.0 |
| Croscarmellose Sodium, NF, Type A | 15.0 |
| Talc USP | 10.0 |

Tablets compressed from this resulting final blended formulation containing approximately 800 mg. of ibuprofen per tablet, and then film coated were found to have the following properties:

| Property | Result |
| --- | --- |
| Disintegration time | 1 minute |
| Dissolution time, for 55% dissolved | 3 minutes |
| Water (Karl Fischer) | 0.9% |

| Property | Result |
| --- | --- |
| Ibuprofen content, per tablet, average | 802 mg. |

Figure 1:
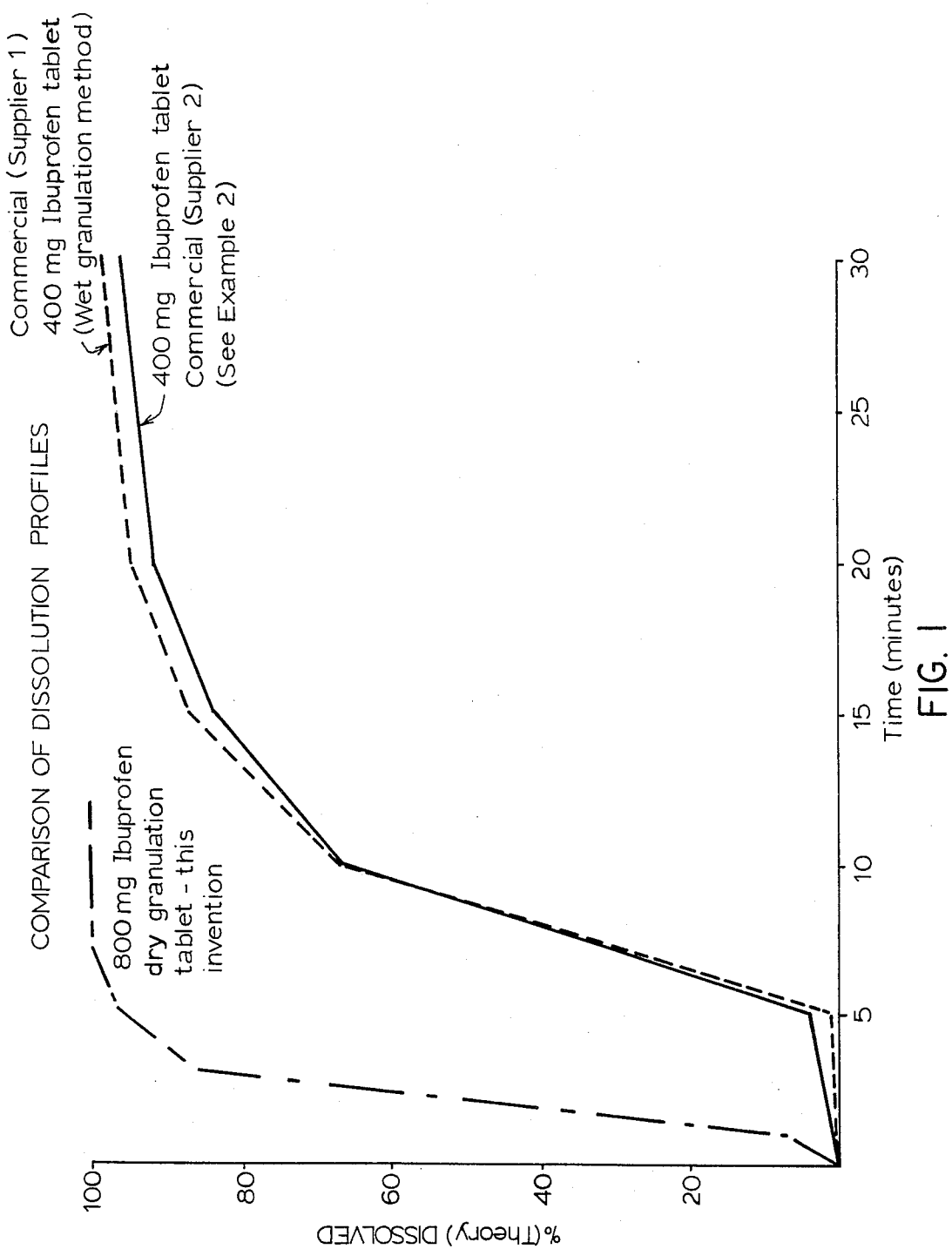

A comparison of the release profiles, using standard USP testing procedures, of these new film coated 800 mg. ibuprofen compressed tablets having the above presented, dry granulation formula with sugar coated 400 mg. ibuprofen compressed tablets from two commercial sources (Suppliers 1 and 2). We know that Supplier 1 used a wet granulation method to make its 400 mg. ibuprofen compressed tablets. The method used by Supplier 2 to make its 400 mg. ibuprofen compressed tablet are unknown, but the results of this test show it to be similar in dissolution properties to the 400 mg. ibuprofen compressed tablet of Supplier 1. (See FIG. 1)

EXAMPLE 3

Effect of Varying Levels of Intragranular Croscarmellose Sodium NF, Type A Disintegrant on Dissolution Rate of Ibuprofen From 800 mg. Ibuprofen Compressed Tablets The effect of increasing levels of disintegrant from compressed tablets containing 800 mg. ibuprofen was studied using a revised USP dissolution test, that is, a 50 RPM basket speed which is more discriminating than the 150 RPM basket speed of the USP test.

This inventigation was designed to improve and optimize the in vitro dissolution rate properties of the 800 mg. ibuprofen compressed tablets of the dry granulation formulation. It was hoped that the addition of increased levels of intragranular disintegrant would improve the 800 mg. ibuprofen tablet's dissolution characteristics. Rotating basket RPM was slowed to 50 RPM during these dissolution rate study test to discern differences in properties of the tableted formulations being tested.

MATERIALS AND METHODS

Dissolution

The dissolution profiles for ibuprofen released from the tablets were collected using a Hanson Multiple Spindle Dissolution Apparatus employing 900 mls. of 0.05M $KH_2PO_4$ dissolution media in each flask. The setup and operation are outlined below:

Water Bath—37° C.
Basket RPM—50 RPM
Flow Rate—45 ml./minute
Wavelength—221.0 nm
Cell Width—0.10 mm (Manual)
Temperature Control—37° C.

The average results of two tablets were used for calculating all data points.

RESULTS AND DISCUSSION

Figure 2:
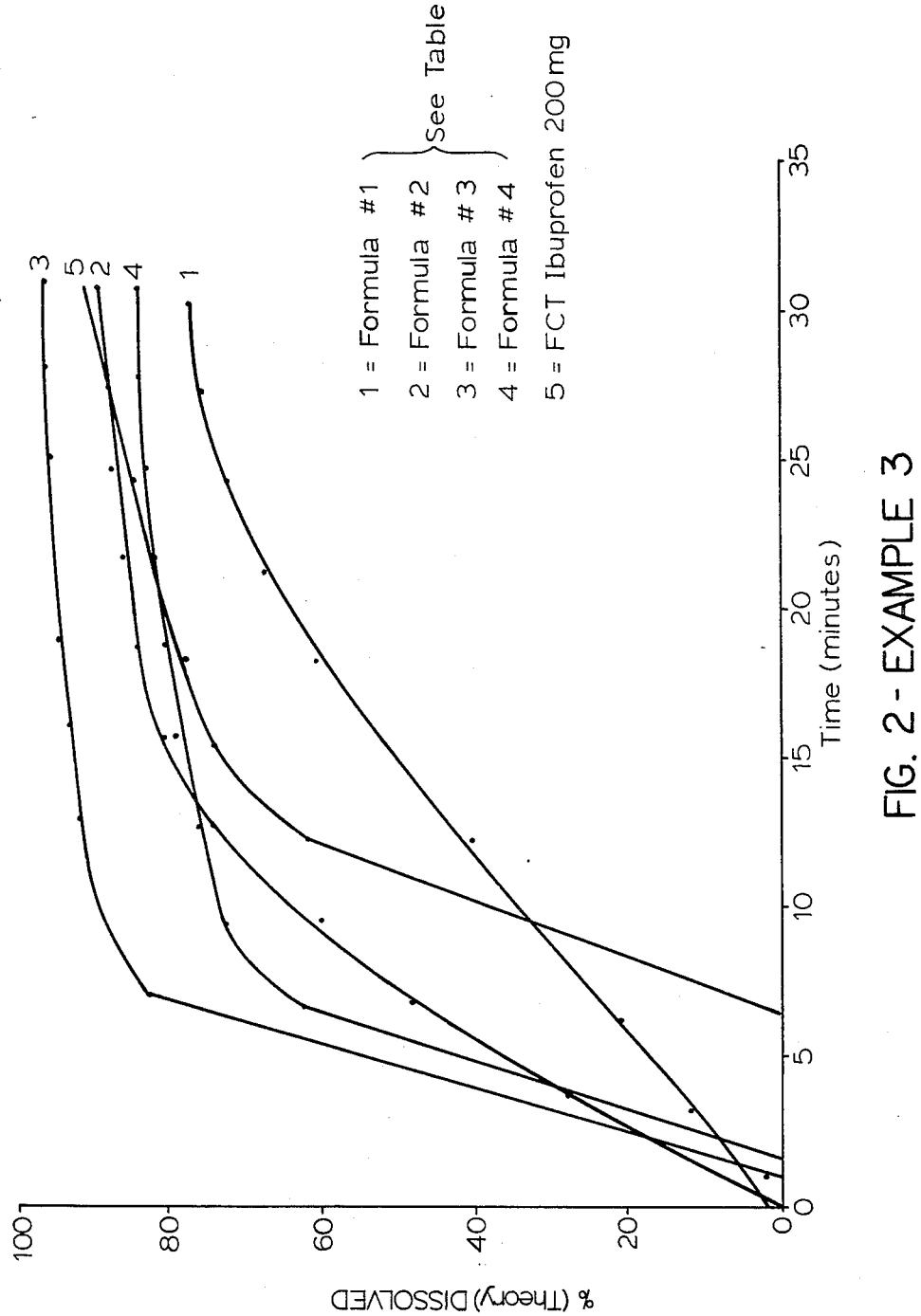

Table I summarizes the formulations tested which contained various levels of intragranular Croscarmellose Sodium NF, Type A. The 11 to 91 mg./compressed tablet shown in Table I equate to percent range of intragranular disintegrant tested of between 1.34 and 10.11% of the total dry granulation weight. Physical properties (i.e., friability, tablet thickness, tablet hardness, etc.) other than dissolution were acceptable for all tablet formulations. FIG. 2 shows the dissolution characteristics of the various formulations at a 50 RPM basket speed. FCT ibuprofen 200 mg. (wet granulation method) dissolution results were included for comparison purposes. It was discovered that there is an optimal concentration (% W/W) of intragranular Croscarmellose Sodium NF, Type A above which the dissolution characteristics become worse. This drop in dissolution rate is most likely due to the formation of a gelatinous layer which tends to prevent complete disintegration of the tablet. This is a common phenomenon, often seen with high levels of other carboxymethylcellulose diluents. At 91 mg. of intragranular disintegrant (Formula 4), the formation of a gelatinous mass was visually observed during the dissolution study.

Figure 3:
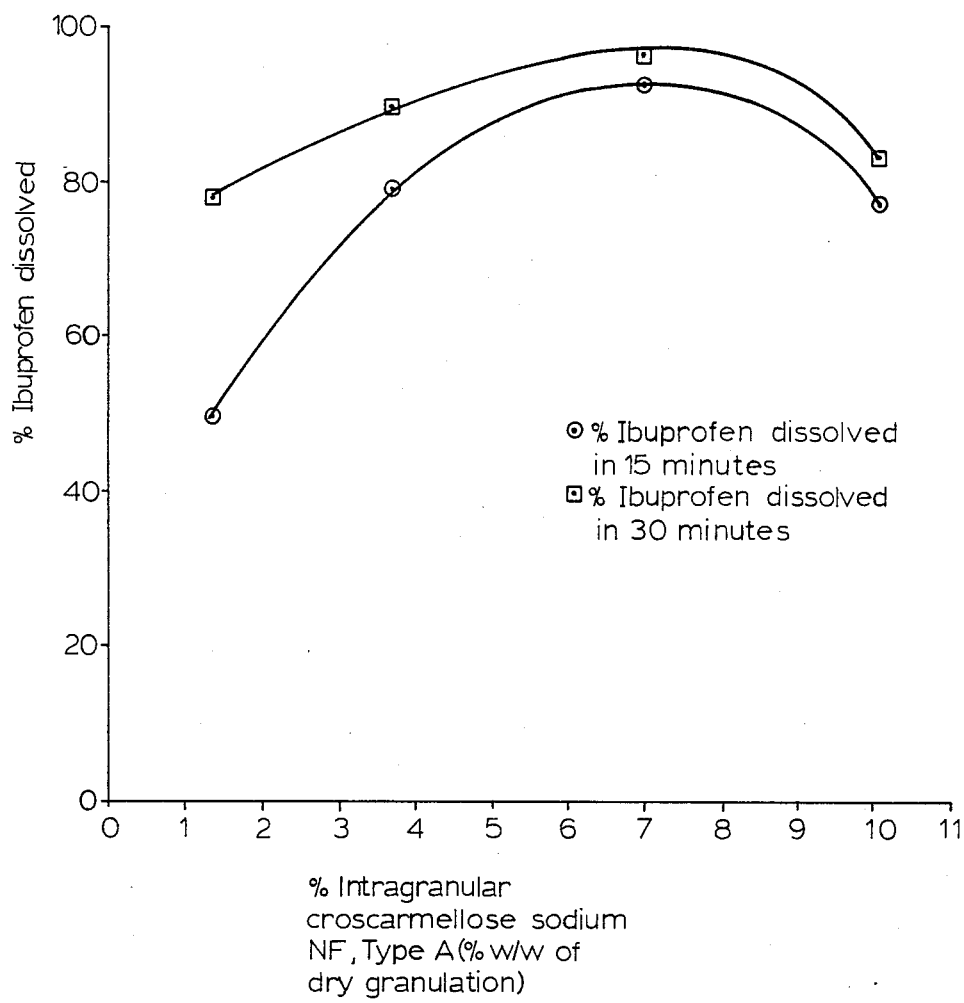
FIG. 3 is an ordinate/abscissa graph showing the effect on the percent drug dissolved at 15 and 30 minutes of various percentages of the intragranular corsslinked sodium carboxymethylcellulose (Croscarmellose Sodium NF, Type A) disintegrant, in 800 mg. ibuprofen (dry granulation) compressed tablet formulations, of this invention. See Example 3.

FIG. 3 graphically depicts the optimal level of intragranular disintegrant to be between about 6 and 8 percent of the total dry granulation weight. At a 7.01% level, the total tablet weight was 1100 mg. and all physical characteristics fell within the proposed specifications for FCT ibuprofen 800 mg.

SUMMARY AND CONCLUSIONS

The above results indicate that the dissolution properties of ibuprofen 800 mg. compressed tablets can be significantly improved through the use of increased levels of intragranular Croscarmellose Sodium NF, Type A. Increasing the intragranular disintegrant level from 1.34 percent to 7.01 percent of the total weight helped improve the dissolution characteristics without adversely affecting other important physical properties (i.e., granulation flow; tablet friability, hardness, thickness, etc.). However, disintegrant levels above 7.01 percent caused a decrease in dissolution properties due to gel formation.

EXAMPLE 4

Relative Bioavailability of Ibuprofen From 800 mg. (Dry Granulation) Tablets: Effect of Intragranular Disintegrant Levels—Blood Level Studies The present study was conducted to assess the effect of varying the quantity of intragranular disintegrant (Croscarmellose Sodium NF, Type A) on the relative bioavailability of FCT ibuprofen 800 mg. (dry granulation). Three FCT 800 mg. ibuprofen formulations which differed only by the amount of intragranular disintegrant were administered as single oral 800 mg. doses to 22 normal human adult volunteers. The disintegrant levels covered an entire range of 11 to 61 mg./tablet. SCT ibuprofen 400 mg. (two tablets) was also administered to each subject. A four-way Latin-square crossover experimental design was employed. SCT means sugar coated compressed tablet.

Varying the amount of intragranular disintegrant in FCT ibuprofen 800 mg. (dry granulation) over the range specified (11 to 61 mg./tablet) had no effect on extent of absorption but did influence the absorption rate, such that bioequivalence with SCT ibuprofen 400 mg. (at equivalent 800 mg. doses) was achieved by those formulations containing 31 to 61 mg./tablet of the excipient.

The reasons for which two subjects did not complete the study were apparently unrelated to the study treatments or procedures. Subject 23 discontinued participation after Phase 1 for what were described as personal reasons. Subject 19 reported "flu" symptoms prior to Phase IV and could not continue the study. Both subbjects were excluded from analyses of the study results.

Study Design

The four study treatments were administered according to a four-way Latin-Square crossover experimental design. The study design and randomization schedule are summarized in the following table:

| Group | Subjects/Group | I | II | III | IV |
|---|---|---|---|---|---|
| 1 | 3,8,9,14,18,22 | A | B | D | C |
| 2 | 5,7,12,13,20,13 | B | C | A | D |
| 3 | 1,4,11,16,19,23 | C | D | B | A |
| 4 | 2,6,10,15,17,21 | D | A | C | B |

Treatment adiministrations were separated by four days. The volunteers were required to fast for nine hours prior to and for four hours following drug administration. During the fasting period no food or beverage other than water was permitted. Water was consumed adlib. The subjects were required to ingest 180 ml. of water at the time of drug adminstration. All concomitant medications were prohibited for seven days prior to and throughout the study period.

During each phase, blood (7 ml.) was collected from the forearm vein by individual venipuncture into Vacutainer blood collection tubes (plain for serum harvest) at the following times relative to drug administration: 0 (prior to dose), 0.333, 0.667, 1, 1.5, 2, 3, 4, 5, 8, 10 and 12 hours. Serum was immediately harvested, frozen and maintained in a frozen state ($-20°$ to $-15°$ C.) until assayed for ibuprofen by HPLC with UV detection.

CALCULATIONS

Bioavailability Parameters

The terminal rate conctants ($\lambda_z$) were estimated by linear least squares regression of $\ln C_t$ vs. t (time) utilizing those data points in the terminal log-linear region of the serum concentration-time curves. Estimates of the calculated serum concentration ($C_T$) at time T, (T is the last sampling time utilized for estimation of $\lambda_z$), were obtained from the same regression equation.

$AUC_{12}$ and $AUC_T$ (Area Under the Curve), areas under the serum concentration-time curve through 12 hours and time T, and $AUMC_T$ (Area Under the Moment Curve), area under the first moment curve through time T, were calculated using trapezoidal rule. $AUC\infty$ and $AUMC\infty$ (areas under the serum concentration-time curve and first moment curve through infinite time), were estimated according to Equations 1 and 2.

$$AUC\infty = AUC_T + \frac{\hat{C}_T}{\lambda_z} \qquad \text{Eq. 1}$$

$$AUMC\infty = AUMC_T + \left[\frac{T + 1}{\lambda_z}\right] \frac{C_T}{\lambda_z} \qquad \text{Eq. 2}$$

The symbol $C_T$ means estimate of serum concentration of T time.

INTRODUCTION

The FCT ibuprofen 800 mg (dry granulation) tested in a previous bioavailability trial was a dry granulation formulation containing 11 mg./tablet Croscarmellose Sodium NF, Type A as an intragranular disintegrant. The study demonstrated that such a formulation was fully bioavailable but somewhat more slowly absorbed than SCT (sugar coated compressed tablet) 400 mg. commercial ibuprofen (wet granulation) tablets at equivalent doses (1).

Subsequent activities indicated that the processability of the dry granulation was improved and the in-vitro dissolution rate of the tablet was increased as the quantity of intragranular disintegrant was increased over the range 11 to 61 mg./tablet (see Example 3). As a result, that range was specified in he formulation description for FCT (film coated compressed tablet) ibuprofen 800 mg. (dry granulation) tablets of this bioequivalence test.

The bioavailability characteristics of three FCT 800 mg. ibuprofen (dry granulation) formulations which differed only by the quantity of intragranular disintegrant were evaluated in the study. The formulations are given as formulas 1, 2 and 3 in Table I. The dry granulation preparations studied covered the entire specified range for that excipient. The objectives of the study were to validate the specification and to determine whether the in-vivo absorption rate could be increased by increasing the intragranular disintegrant levels, a hypothesis suggested by the in-vitro dissolution results.

EXPERIMENTAL

Dosage Forms Studied

During the study the following tratments were adminstered as single oral doses:

Treatment A: 1 FCT ibuprofen 800 mg. tablet (dry granulation) (11 mg. intragranular disintegrant)

Treatment B: 1 FCT ibuprofen 800 mg. tablet (dry granulation) (31 mg. intragranular disintegrant)

Treatment C: 1 FCT ibuprofen 800 mg. tablet (dry granulation) (61 mg. intragranular disintegrant)

Treatment D: 2 SCT ibuprofen 400 mg. tablets (wet granulation, commercial)

Human Subjects

Twenty-four (24) normal healthy human adult volunteers were selected to participate in the trial. They were accepted into the study following informed consent, physical examination and blood and urine analysis. Twenty-two (22) subjects successfully completed all four phases of the study. They were 11 males and 11 females who ranged in age from 19 to 40 years (mean=24 years) and in body weight from 42 to 89 kg. (mean=71 kg.). A summary of the individual subject characteristics is presented in Table III.

Mean residence time (MRT) was calculated using Equation 3.

$$MRT = AUMC_\infty / AUC_\infty \qquad Eq.3$$

Statistical Comparisons

Prior to statistical evaluations the ibuprofen blood serum concentrations and bioavailability parameters where normalized to an 800 mg. dose based on reported assay potency of the product lots used in the study. Statistical analyses were performed using a mixed effects analysis of variance model with group, period and treatment as fixed effects, and subject within group as a random effect. The Waller-Duncan k-ratio t-test and utilized for pairwise comparisons of treatment means.

Results and Discussion

The mean ibuprofen serum concetrations and related paramerters resulting from administration of each treatment are presented in Table IV along with the results of statistical comparisons of the treatment means. Cartesian plots of means ibuprofen serum concentration vs. time for the four treatments, A, B, C and D are shown in FIG. 9.

Comparisons of mean ibuprofen serum conectrations at individual sampling times revealed statistically significant differences among the treatments at each time. Most of those differences could be associated with pairwise comparisons between Treatment A and the remaining three treatments. Generally, Treatment A resulted in lower mean ibuprofen levels through the two hour sampling time and greater levels thereafter than the other treatments. That pattern of differences suggested that Treatment A was the most slowly absorbed of the treatments evaluated.

The four treatments resulted in nearly identical mean areas under the concentration-time curve through 12 hours and infinite time, indicating that variations in the quantity of intragranular disintegrant over the range 11 to 61 mg./tablet had no adverse influence on the amount of the ibuprofen absorbed from the dosage forms. Additionally, it demonstrated that all three FCT 800 mg. ibuprofen (dry granulation) formulations were fully bioavailable relative to the commercial SCT ibuprofen 400 mg. at equivalent doses.

Statistically significant differences among the treatments were detected for those parameters indicative of absorption rate, i.e., peak concentration, peak time and mean residence time. Treatment A was somewhat more slowly absorbed than all of the remaining treatment as indicated by significant differences for all three parameters. Based upon small but statistically significant differences in peak concentration, Treatment B was very slightly more slowly absorbed than Treatments C and D. No differences with respect to absorption rate could be discerned between Treatments C and D. Note that at times less than one hour, the serum levels of ibuprofen for Treatment C are significantly higher statistically than for Treatment D indicating initial rapid absorption of ibuprofen from tablets manufactured from this invention (Table IV). The B vs. C and B vs. D differences were sufficiently small that Treatments B, C and D may be considered bioequivalent. See FIG. 9.

Conclusion

Varying the amount of intragranular disintegrant to FCT ibuprofen (dry granulation) 800 mg. over the range specified (11 to 61 mg./tablet) had no effect on extent of absorption but did influence the absorption rate, such that bioequivalence with the commercial SCT ibuprofen 400 mg. (at equivalent 800 mg. doses) was achieved by those formulations containing 31 and 61 mg./tablet of that excipient.

EXAMPLE 5

Formulation for Capsules

The following two major parts (dry granulation part and extragranular excipient part) formula was prepared as described hereinbelow as a proposed drug delivery system for a 200 mg. ibuprofen capsule filling formulation:

Dry Granulation Part:
Ibuprofen USP 200 mg.
Collolidal Silicon Dioxide, NF 2 mg.
Croscarmellose, Sodium NF, Type A 15.25 mg.
Magnesium Stearate NF (Powder, Food Grade) 0.25 mg.
Extragranular Excipients:

Magnesium Stearate NF (Powder, Food Grade) 6.0 mg.

Mineral Oil USP (Viscosity 180 cps) 8.0 mg.

Microcrystalline Cellulose NF (Medium Powder) 107.1 mg.

Pregelatinized Starch NF 71.4 mg.

The above-listed materials under Dry Granulation are mixed in bulk in the above proportions for the number of proposed capsule dosages to be made per batch in the equipment available.

These mixed dry granulation excipients and drug are then roller compacted or slugged, milled and sieved to form uniform granules. The dry mix granules are then added to the extragranular excipients in a V-blender and mixed. The mixed material is then filled into capsules using the appropriate equipment. Dissolution testing on these capsules using the USP basket methodology was performed. The results are given below.

| Time (min) | Range % Dissolved | Relative Standard Deviation % |
|---|---|---|
| 5 | 91.20–95.08 | 1.54 |
| 10 | 95.36–101.74 | 2.17 |
| 15 | 96.12–103.21 | 2.36 |
| 20 | 96.49–103.58 | 2.36 |
| 25 | 96.49–103.77 | 2.41 |
| 30 | 96.49–103.77 | 2.43 |

These results again indicate the excellent dissolution properties from the dry granulation of this invention.

EXAMPLE 6

EFFECT OF ACCELERATED AGING ON DISINTEGRATION AND DISSOLUTION OF TWO COMMERCIAL IBUPROFEN LOTS OF SUPPLIERS (1) AND (2) WITH IBUPROFEN DRY GRANULATION LOT OF THIS INVENTION (3)

This brief study was designed to determine the effect of extreme aging conditions on the disintegration and dissolution rate of FCT ibuprofen (from the dry granulation process of this invention) 800 mg. (3) and FCT ibuprofen 600 mg. from a commercial "wet granulation" method from two different suppliers (1, 2).

It is well known that ibuprofen tablets manufactured using the "current" commercially used wet granulation formula tend to "age" at accelerated conditions. The aging phenomenon manifests itself as a decrease in the percentage of drug dissolved over time. This study examines the aging phenomenon using a dissolution test which appears to be rank order correlated to in vivo bioavailiability for ibuprofen 800 mg.

MATERIALS AND METHODS

The tablets used in this study were from the following lots:

Product Lots

1. FCT ibuprofen 600 mg. (Upjohn)—Product 1
2. FCT ibuprofen 600 mg. (Boots)—Product 2
3. FCT ibuprofen 800 mg. (dry granulation—this invention)—Product 3

FCT means film coated compressed tablet.

After initial dissolution testing, the tablets were placed in open petri dishes in a 60° C. oven. Tablets were sampled at specified time points. The dissolution test employed was described in detail in Example 3 hereinabove.

Basically, it employs a 50 RPM rotating basket instead of the currently used USP 150 RPM basket. The average of two individual tablets was used for calculating data points. At the end of the initial dissolution runs, the basket RPM was increased to 250 RPM until all drug was in solution. No significant differences existed between the drug concentration at 100% dissolution and the labeled amounts when compared to a series of standard solutions.

RESULTS AND DISCUSSION

Figure 4:
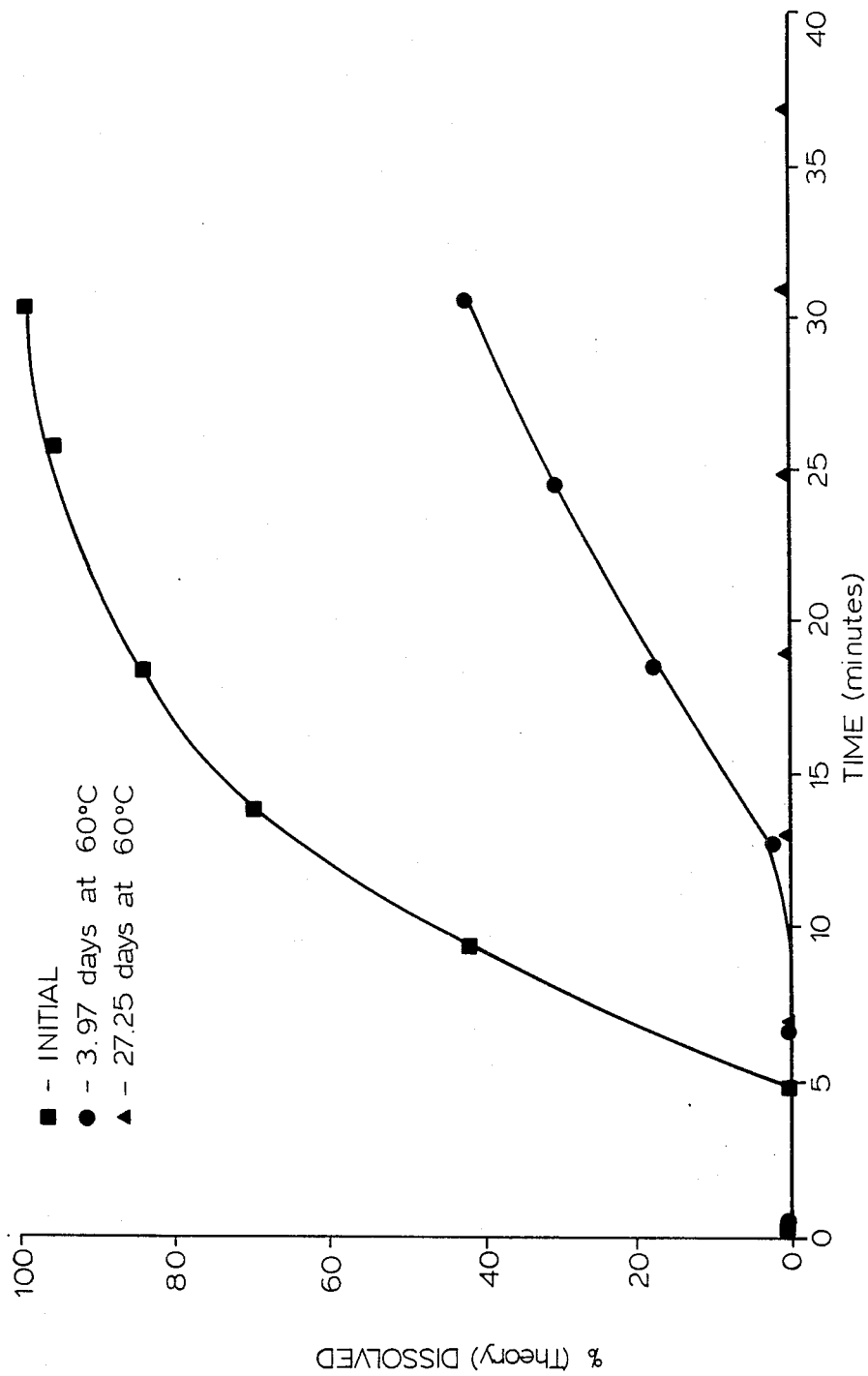
FIG. 4 is an ordinate/abscissa graph depicting the effect of aging of the tablets at 60° C. on dissolution rate of 600 mg. ibuprofen compressed tablets ("wet granulation", commercial) (Product 1).

FIG. 4 shows the results of "aging" on the dissolution profile (at 50 RPM basket speed) for compressed, coated ibuprofen 600 mg. (Product 1). After 3.97 days at 60° C. in open petri dishes, the dissolution rate is drastically reduced. After 27.25 days, no drug dissolved from the tablets. Visual inspection during the dissolution run revealed that the tablets did not disintegrate. Also, the film coat remained intact on the tablets.

Figure 5:
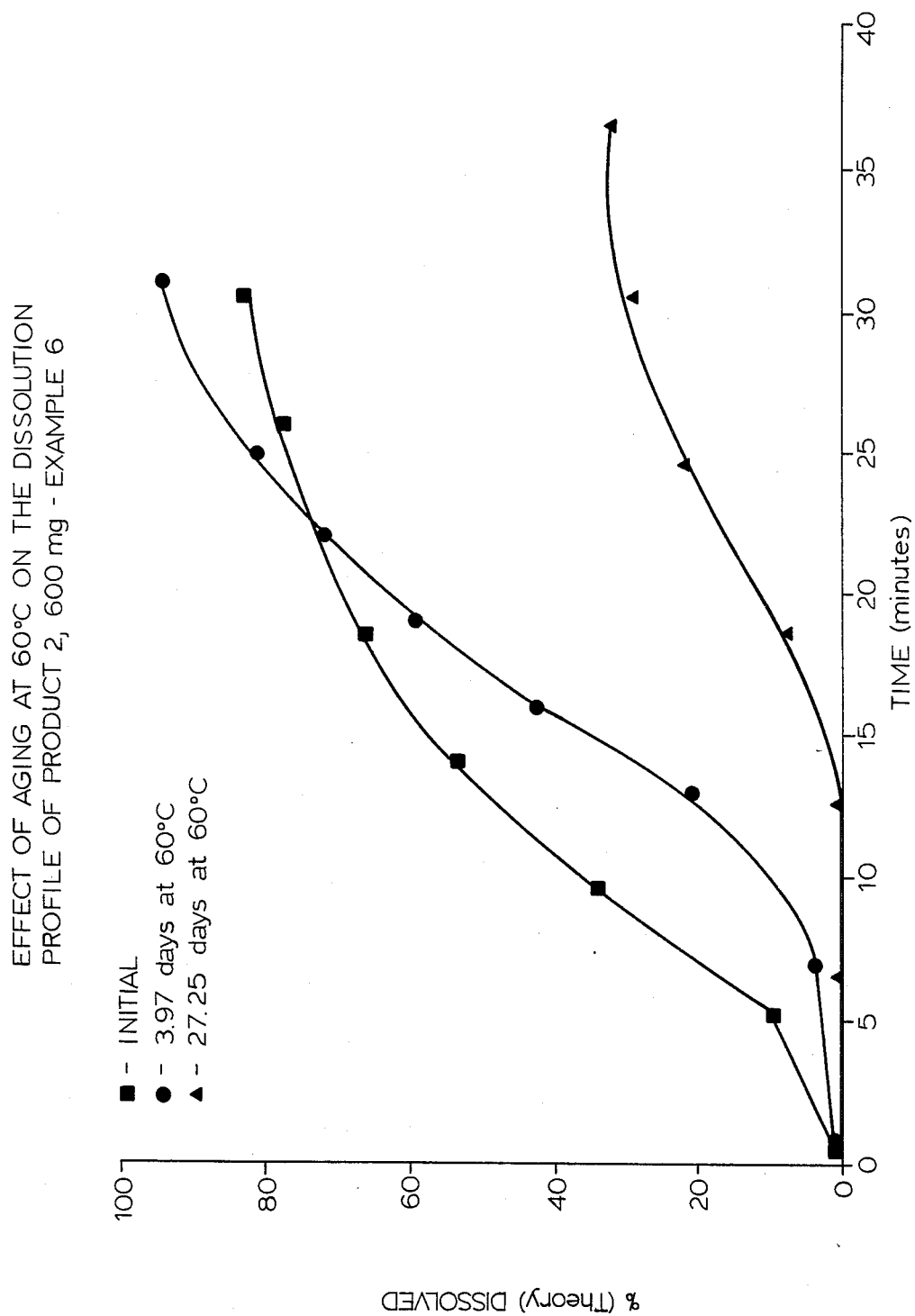
FIG. 5 is an ordinate/abscissa graph depicting the effect of 60° C. aging of commercial 600 mg. compressed ibuprofen tablets, commercially available (Product 2).

FIG. 5 shows the results of aging on the dissolution rate of FCT ibuprofen 600 mg. (Product 2) tablets. After 3.97 days at 60° C., the ibuprofen tablets showed only slight effects of the aging. After 27.25 days at 60° C., Product 2 ibuprofen tablets dissolution rate dropped dramatically.

Figure 6:
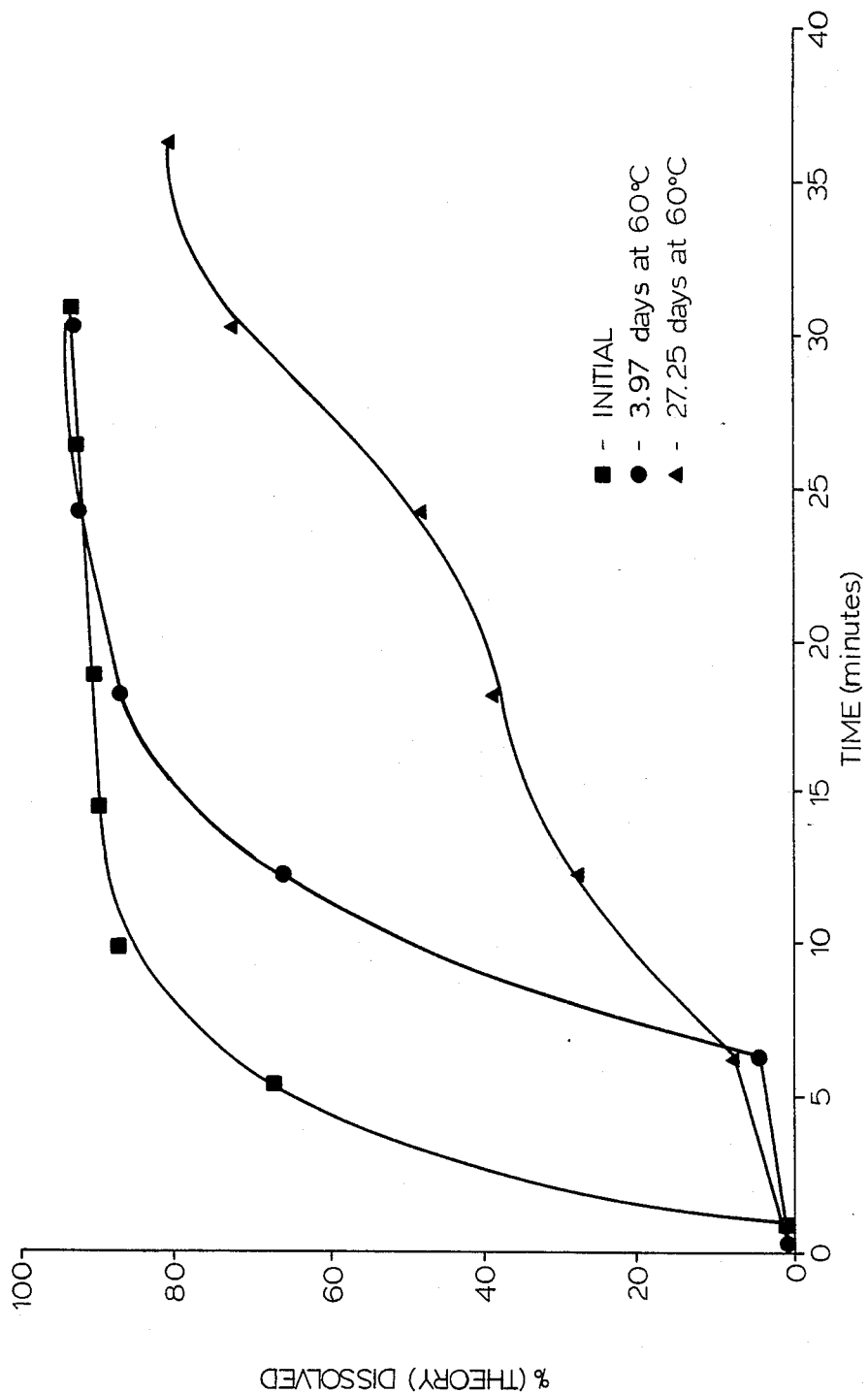
FIG. 6 is an ordinate/abscissa graph depicting the effect of 60° C. aging of 800 mg. ibuprofen (dry granulation) formulation compressed tablets (Product 3) of this invention.

FIG. 6 shows the results of aging on the dissolution of FCT ibuprofen (dry granulation) 800 mg. tablets (Product 3—this invention). After 3.97 days at 60° C., the dissolution profile is minimally affected. After 27.25 days the dissolution rate profile was lower, but is still significantly better than the other two commercial ibuprofen products (Products 1 and 2 hereinabove).

Table II summarizes the results of the dissolution runs comparing the percent ibuprofen dissolved in 30 minutes for the Products (1), (2) and (3) studied in this Example.

SUMMARY AND CONCLUSIONS

The results indicate that under the specified aging conditions the new 800 mg. ibuprofen dry granulation formulation of this invention (Product 3) is superior to both of the commercial ibuprofen 600 mg. formulations (Products 1 and 2) with respect to dissolution properties. The results indicate that minimal scintering of ibuprofen on aging at accelerated conditions (60° C.) is apparent for Product 3 (the 800 mg. ibuprofen dry granulation formulation of this invention) when compared to the effect of similar aging of the two commercial wet granulation derived ibuprofen 600 mg. tableted formulations.

TABLE I

| GRANULATION INGREDIENTS (MG./CT)* (See Example 3) | | | | |
|---|---|---|---|---|
| Formula Number | Ibuprofen USP | Colloidal Silicon Dioxide NF | Magnesium Stearate NF Powder Food Grade | Croscarmellose Sodium NF, Type A |
| 1 | 800 | 8 | 1 | 11 |
| 2 | 800 | 8 | 1 | 31 |
| 3 | 800 | 8 | 1 | 61 |
| 4 | 800 | 8 | 1 | 91 |

*Running powder for all formulas consisted of Croscarmellose Sodium NF, Type A (15 mg./CT), Microcrystalline Cellulose NF Coarse Powder (190 mg/CT), Colloidal Silicon Dioxide NF (15 mg./CT), and Talc USP No. 141 (10 mg./CT). The lot numbers for all ingredients were held constant throughout the study. Croscarmellose Sodium NF, Type A has a tradename of Ac-Di-Sol TM of Farm Machinery Corporation for a cross-linked sodium carboxymethylcellulose, available to pharmaceutical manufacturers.

TABLE II (Example 6)
Comparison of Percent Ibuprofen Dissolved in 30 Minutes

| Time at 60° C. | (1) Upjohn Ibuprofen Commercial FCT 600 Mg. | (2) Ibuprofen Boots 600 Mg. | (3) FCT Ibuprofen (New Dry Granulation) 800 Mg. |
|---|---|---|---|
| Initial | 99% | 82% | 93% |
| 3.97 days | 42% | 93% | 94% |
| 27.25 days | 0% | 30% | 70% |

TABLE III

Summary of Individual Subject Characteristics
(Example 4)

| SUBJECT | SEX | RACE | AGE IN YEARS | WEIGHT (LBS.) | HEIGHT (INCHES) | WEIGHT (KGS.) |
|---|---|---|---|---|---|---|
| 1 | M | W | 19 | 196 | 73 | 88.9 |
| 2 | F | W | 40 | 139 | 64 | 63.0 |
| 3 | M | W | 23 | 182 | 68 | 82.6 |
| 4 | F | W | 27 | 144 | 64 | 65.3 |
| 5 | M | W | 26 | 161 | 70 | 73.0 |
| 6 | F | W | 23 | 138 | 65 | 62.6 |
| 7 | M | W | 21 | 150 | 69 | 68.0 |
| 8 | F | W | 23 | 93 | 63 | 42.2 |
| 9 | M | W | 21 | 161 | 67 | 73.0 |
| 10 | F | W | 24 | 159 | 67 | 72.1 |
| 11 | M | W | 23 | 190 | 73 | 86.2 |
| 12 | F | W | 23 | 152 | 67 | 68.9 |
| 13 | M | W | 21 | 170 | 72 | 77.1 |
| 14 | F | W | 20 | 141 | 66 | 64.0 |
| 15 | M | W | 19 | 155 | 68 | 70.3 |
| 16 | F | W | 21 | 108 | 63 | 49.0 |
| 17 | M | W | 19 | 168 | 70 | 76.2 |
| 18 | F | W | 20 | 168 | 69 | 76.2 |
| 20 | F | W | 27 | 177 | 70 | 80.3 |
| 21 | M | W | 26 | 175 | 73 | 79.4 |
| 22 | F | W | 26 | 141 | 65 | 64.0 |
| 24 | M | W | 30 | 192 | 72 | 87.1 |
| Average | | | 23.7 | 157.3 | 68.1 | 71.3 |
| Minimum | | | 19.0 | 93.0 | 63.0 | 42.2 |
| Maximum | | | 40.0 | 196.0 | 73.0 | 88.9 |

The distribution of the subjects by race was:

|   | M | F |
|---|---|---|
| W | 11 | 11 |
| W | 0 | 0 |

TABLE IV

MEAN IBUPROFEN SERUM CONCENTRATIONS AND RELATED PARAMETERS RESULTING FROM THE ADMINISTRATION OF SINGLE ORAL 800 MG. DOSES OF IBUPROFEN TO 22 NORMAL ADULT VOLUNTEERS++

| Ibuprofen Serum Concentration At: Hour: | Treatment A (11 mg. Intragranular Disintegrant (Dry Granulation) (Mcg./ml.) | Treatment B (31 mg. Intragranular Disintegrant (Dry Granulation) (Mcg./ml.) |
|---|---|---|
| 0 | 0.00 | 0.00 |
| 0.333 | 7.65 | 15.3 |
| 0.667 | 17.0 | 27.8 |
| 1 | 24.0 | 36.4 |
| 1.5 | 34.7 | 47.3 |
| 2 | 41.3 | 47.6 |
| 3 | 43.5 | 39.3 |
| 4 | 35.7 | 28.2 |
| 6 | 15.1 | 11.5 |
| 8 | 6.66 | 5.16 |
| 10 | 3.37 | 2.66 |
| 12 | 1.68 | 1.05 |
| Peak Concentration (mcg./ml.) | 47.6 | 54.3 |
| Peak Time (h) | 2.7 | 1.9 |
| Average Area Under Conc. - Time Curve (mcg./h/ml.) | | |
| 0-12 h | 216 | 210 |
| 0-∞ | 222 | 215 |
| Mean Residence Time (hours) | 4.12 | 3.53 |
| Terminal Rate Constant ($h^{-1}$) | 0.348 | 0.366 |
| Terminal Half-life (hours) (harmonic mean) | 1.99 | 1.89 |

| Ibuprofen Serum Concentration At: Hour: | Treatment C 1 FCT 800 Mg. (61 Mg. Intragranular Disintegrant) (Dry Granulation) (Mcg./Ml.) | Treatment D 2 SCT 400 Mg. (Commercial) (Wet Granulation) (Mcg./Ml.) |
|---|---|---|
| 0 | 0.00 | 0.00 |
| 0.333 | 24.0 | 4.45 |
| 0.667 | 41.7 | 29.1 |
| 1 | 48.8 | 40.2 |
| 1.5 | 51.7 | 55.0 |
| 2 | 47.2 | 55.2 |
| 3 | 37.0 | 40.2 |
| 4 | 26.6 | 27.5 |
| 6 | 10.3 | 10.6 |
| 8 | 4.90 | 4.87 |
| 10 | 2.22 | 2.27 |
| 12 | 1.11 | 0.98 |
| Peak Concentration (Mcg./ml.) | 58.7 | 61.7 |
| Peak Time (hours) | 1.5 | 1.8 |
| Average Area Under Conc. - Time Curve (mcg./h/ml.) | | |
| 0-12 h | 216 | 215 |
| 0-∞ | 221 | 219 |
| Mean Residence Time (hours) | 3.27 | 3.42 |
| Terminal Rate Constant ($h^{-1}$) | 0.364 | 0.369 |

TABLE IV-continued

MEAN IBUPROFEN SERUM CONCENTRATIONS AND RELATED PARAMETERS RESULTING FROM THE ADMINISTRATION OF SINGLE ORAL 800 MG. DOSES OF IBUPROFEN TO 22 NORMAL ADULT VOLUNTEERS[++]

| | | |
|---|---|---|
| Terminal Half-life (hours) (harmonic mean) | 1.91 | 1.88 |

| Ibuprofen Serum Concentration At: Hour: | ANOVA[+] (Among Treatments) | Pairwise Comparisons[**] | | | | | |
|---|---|---|---|---|---|---|---|
| | | A & B | A & C | A & D | B & C | B & D | C & D |
| 0 | — | — | — | — | — | — | — |
| 0.333 | <.0001* | + | + | − | + | + | + |
| 0.667 | <.0001* | + | + | + | + | − | + |
| 1 | <.0001* | + | + | + | + | − | − |
| 1.5 | <.0001* | + | + | + | − | + | − |
| 2 | <.0001* | + | + | + | − | + | + |
| 3 | .038* | − | + | − | − | − | − |
| 4 | <.0001* | + | + | + | − | − | − |
| 6 | <.0001* | + | + | + | − | − | − |
| 8 | <.0001* | + | + | + | − | − | − |
| 10 | <.0001* | + | + | + | − | − | − |
| 12 | .0069* | + | + | + | − | − | − |
| Peak Concentration (mcg./ml.) | <.0001* | + | + | + | + | + | − |
| Peak Time (hours) | <.0001* | + | + | + | − | − | − |
| Average Area Under Conc. - Time Curve (mcg./h/ml.) | | | | | | | |
| 0–12 h | .45 | — | — | — | — | — | — |
| 0–∞ | .45 | — | — | — | — | — | — |
| Mean Residence Time (hours) | <.0001* | + | + | + | − | − | − |
| Terminal Rate Constant (h$^{-1}$) | .71 | — | — | — | — | — | — |

[+] = Analysis of Variance for Complete Crossover Design, Level of Significance
[++] = Values normalized to an 800 mg. dose based on assay potency.
* = Statistically significant (p ≦ .05) differences among treatment means
** = Waller-Duncan k-ratio t-test; tested only at the 95% confidence level; (+) = (p ≦ .05), (−) = (p > .05)

I claim:

1. A phamaceutical, high drug content ibuprofen dry granulation formulation composition comprising
   (a) about 85 to 99 percent, W/W of ibuprofen
   (b) about 1 to 15 percent of croscarmellose sodium NF, types A and/or B,
   the percentages of each ingredient (a) and (b) being based upon the weight of the total granulate formulation.

2. An ibuprofen granulation formulation according to claim 1 which further includes from 0.4 to 1 percent of colloidal silicon dioxide NF, based upon the weight of the total granulation formulation.

3. An ibuprofen granulation formulation according to claim 1 prepared by (1) dry mixing (a) ibuprofen and (b) croscarmellose sodium NF containing mixture to an essentially uniform consistency,
   (2) roller compacting or slugging the mixture from step (1), and
   (3) sizing the compacted or slugged mixture from step (2) to form a granular ibuprofen composition.

4. A pharmaceutical granulation composition useful for making therefrom extensive numbers of ibuprofen containing compressed tablets or filled pharmaceutical capsules having dosage ranges of from about 100 to 1200 mg. of ibuprofen per compressed tablet or filled capsule which comprises (A) a granulate formulation containing ibuprofen and croscarmellose sodium type A as described in claims 1 or 2 and optionally mixed with the following extragranular part (B) ingredients:

| Ingredient | Mg. per tablet or capsule dosage unit |
|---|---|
| Croscarmellose sodium NF, type A | 0 to 25 |
| Microcrystalline cellulose, NF | 0 to 225 |
| Talc USP | 0 to 25 |
| to a uniform consistency. | |

5. A pharmaceutical ibuprofen dry granulate composition according to claim 4 adapted for making extensive numbers of compressed tablets therefrom, each compressed tablet containing approximately 800 mg. of ibuprofen which comprises (a) a dry granulate composition containing the following ingredients:

| Ingredient | Amount to Equal Mg./Tablet |
|---|---|
| Ibuprofen | 720 to 880 |
| Croscarmellose sodium NF, Type A | 54 to 67 |
| Colloidal silicon dioxide NF | 7 to 9 |
| Magnesium stearate | 0.5 to 1.5 | which dry granulate compositions (a) is then further mixed to essentially uniform consistency with

| Ingredient | Amount to Equal Mg./Tablet |
|---|---|
| Croscarmellose sodium NF, Type A | 13 to 17 |
| Microcrystalline cellulose, NF | 170 to 210 |
| Colloidal silicon dioxide, NF and | 13 to 17 |
| Talc | 8 to 12 |

6. A pharmaceutical ibuprofen dry granulate composition according to claim 4 adapted for making extensive numbers of compressed tablets therefrom, each compressed tablet containing approximately 1000 mg. of ibuprofen, which comprises (A) a dry granulate composition containing the following ingredients:

| Ingredient | Amount to Equal Mg./Tablet |
|---|---|
| Ibuprofen USP | 900 to 1100 mg. |
| Croscarmellose sodium NF, Type A | 68 to 84 mg. |
| Colloidal Silicon Dioxide, NF | 9 to 11 |
| Magnesium Stearate | 0.75 to 1.75 | which dry granulate composition (A) is then further mixed to essentially uniform consistency with

| Ingredient | Amount to Equal Mg./Tablet |
|---|---|
| Croscarmellose Sodium NF, Type A | 13 to 17 |
| Colloidal Silicon Dioxide NF and | 3 to 7 |
| Talc NF | 10 to 15 |
| to a uniform consistency. | |

7. A pharmaceutical ibuprofen dry granulate composition according to claim 4, adapted for filling into extensive numbers of gelatin capsules, each capsule to contain approximately 200 mg. of ibuprofen which comprises:

(A) a dry granulate composition containing the following ingredients:

| Ingredient | Amount to Equal Mg./Capsule |
| --- | --- |
| Ibuprofen USP | 190 to 210 |
| Croscarmellose Sodium NF Type A | 13.5 to 16.5 |
| Colloidal Silicon Dioxide, NF | 1.5 to 2.5 |
| Magnesium Stearate NF (Powder, Food Grade) | 0.23 to 0.3 | which dry granulate composition (A) is then further mixed with the following additional extragranular ingredients:

| Ingredient | Amount to Equal Mg./Capsule |
| --- | --- |
| Magnesium stearate, NF (powder, food grade) | 5 to 7 |
| Mineral Oil USP | 6 to 8 |
| Microcrystalline cellulose NF | 100 to 110 |
| Pregelatinized starch NF | 60 to 80 | to a uniform consistency.

8. A process for preparing a pharmaceutical ibuprofen granulate composition, which is useful for preparing compressed tablets or filled capsules containing from 100 to 1200 mg. of ibuprofen per dosage unit which comprises:
(1) dry mixing a composition containing ibuprofen and croscarmellose sodium NF, Type A or B, in proportions of from about 85 to 99 percent, W/W of ibuprofen based upon the weight of the total mixture, to about 1 to about 15 percent, W/W of croscarmellose sodium NF, based upon the weight of this mixture to essentially uniform consistency,
(2) passing the mixture from step (1) through a roller compactor or slugging the composition from step (1), and
(3) sizing the resulting compacted or slugged composition from step (2) to form a granulate of essentially uniform size.

9. A process according to claim 8 wherein the composition being dry mixed in step (1) further includes from 0.4 to 1 percent W/W of colloidal silicon dioxide, based on the weight of the total composition being mixed.

* * * * *